US008189800B2

(12) United States Patent
Togawa et al.

(10) Patent No.: US 8,189,800 B2
(45) Date of Patent: May 29, 2012

(54) ACTIVE SILENCER AND METHOD FOR CONTROLLING ACTIVE SILENCER

(75) Inventors: Taro Togawa, Kawasaki (JP); Takeshi Otani, Kawasaki (JP); Kaori Endo, Kawasaki (JP); Yasuji Ota, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 269 days.

(21) Appl. No.: 12/724,237

(22) Filed: Mar. 15, 2010

(65) Prior Publication Data

US 2010/0172511 A1 Jul. 8, 2010

Related U.S. Application Data

(63) Continuation of application No. PCT/JP2007/001033, filed on Sep. 21, 2007.

(51) Int. Cl.
*A61F 11/06* (2006.01)
*G10K 11/16* (2006.01)
*H03B 29/00* (2006.01)

(52) U.S. Cl. .................... 381/71.14; 381/71.8; 381/71.9

(58) Field of Classification Search ...... 381/71.1–71.14, 381/94.1–94.3, 94.7–94.8; 181/206
See application file for complete search history.

(56) References Cited

U.S. PATENT DOCUMENTS

| | | | | |
|---|---|---|---|---|
| 5,293,578 | A | 3/1994 | Nagami et al. | |
| 5,410,606 | A * | 4/1995 | Imai et al. | 381/71.14 |
| 5,982,901 | A | 11/1999 | Kane et al. | |
| 5,991,418 | A | 11/1999 | Kuo | |
| 6,097,823 | A | 8/2000 | Kuo | |
| 6,198,828 | B1 | 3/2001 | Kuo | |
| 6,418,227 | B1 | 7/2002 | Kuo | |
| 6,522,753 | B1 * | 2/2003 | Matsuzawa et al. | 381/71.1 |
| 6,690,805 | B1 * | 2/2004 | Tsuji et al. | 381/94.1 |
| 7,436,968 | B2 * | 10/2008 | Ozawa | 381/71.11 |
| 7,697,699 | B2 * | 4/2010 | Ozawa | 381/94.1 |
| 2005/0234715 | A1 | 10/2005 | Ozawa | |
| 2009/0262951 | A1 * | 10/2009 | Togawa et al. | 381/71.1 |

(Continued)

FOREIGN PATENT DOCUMENTS

JP 2-216906 8/1990

(Continued)

OTHER PUBLICATIONS

Japanese Office Action mailed Nov. 22, 2011 issued in corresponding Japanese Patent Application No. 2009-532969.

(Continued)

*Primary Examiner* — Xu Mei
(74) *Attorney, Agent, or Firm* — Staas & Halsey LLP

(57) ABSTRACT

An active silencer includes: a speaker generating control sound which interferes with noise; a microphone detecting noise remaining after the interference as a remaining noise signal; a sound quality evaluation unit evaluating the sound quality of the remaining noise and output a result of the sound quality evaluation; an actuation signal determination unit determining, according to the result of the sound quality evaluation, the detection timing of the frequency component of the remaining noise signal to be used when the control sound is generated for a plurality of bands of the remaining noise, corresponding to the plurality of bands of a reference signal corresponding to the noise; and a control signal generation unit generating and output a control signal for generation of the control sound depending on a plurality of bands of the determined remaining noise signal and a plurality of bands of the reference signal corresponding to the noise.

9 Claims, 15 Drawing Sheets

U.S. PATENT DOCUMENTS

| | | | | |
|---|---|---|---|---|
| 2010/0002892 | A1* | 1/2010 | Togawa et al. | 381/71.12 |
| 2010/0260353 | A1* | 10/2010 | Ozawa | 381/94.3 |

FOREIGN PATENT DOCUMENTS

| | | |
|---|---|---|
| JP | 3-50998 | 3/1991 |
| JP | 5-218805 | 8/1993 |
| JP | 6-350466 | 12/1994 |
| JP | 8-69288 | 3/1996 |
| JP | 2517150 | 4/1996 |
| JP | 10-190589 | 7/1998 |
| JP | 2872545 | 1/1999 |
| JP | 11-259078 | 9/1999 |
| JP | 0 629 054 B1 | 9/2002 |
| JP | 2002-369281 | 12/2002 |
| JP | 1 587 064 A1 | 10/2005 |
| JP | 2005-303681 | 10/2005 |

OTHER PUBLICATIONS

B. Widrow et al.; Adaptive Signal Processing; Prentice-Hall; 1985; pp. 270-301.

International Search Report for PCT/JP2007/001033, mailed Dec. 18, 2007.

* cited by examiner

ACTIVE SILENCER AND METHOD FOR CONTROLLING ACTIVE SILENCER

CROSS-REFERENCE TO RELATED APPLICATION

This application is a continuation application of International PCT Application No. PCT/JP2007/001033, filed on Sep. 21, 2007, the entire contents of which are incorporated herein by reference.

FIELD

The present invention relates to an active silencer and a method for controlling the active silencer.

BACKGROUND

Active noise control (ANC) is one of the techniques for silencing noise. The ANC is the technology of silencing noise by interfering with noise using sound waves (control sound) with an equal amplitude and an inverse phase.

Recently, an active silencer is used to silence noise of an air-conditioner, in a factory, in a vehicle, etc.

Described below are typical conventional active silencers.

The patent document 1 discloses an active silencer having high silencing performance with low computational complexity. The active silencer is configured by a sensor microphone 101, an FIR filter 102 that can be set with a variable filter coefficient, an FIR filter 103 with a fixed filter coefficient, an LMS arithmetic unit 104 provided at the stage after the FIR filter 103, a controlling speaker 105, and an error microphone 106 as illustrated in FIG. 11. An adaptive filter 107 is configured by the FIR filter 102, the FIR filter 103, and the LMS (least mean square) arithmetic unit 104.

The sensor microphone 101 detects a signal (reference signal) corresponding to noise, and outputs the signal to the FIR filter 102 that can be set with a variable filter coefficient and the FIR filter 103 having a fixed filter coefficient.

The FIR filter (filter of an error path) 103 having a fixed coefficient holds input reference signals x(t) both at the current time and in the past for the number of its taps. The signal (filter reference signal) r(t) obtained by convoluting the propagation function $w\hat{}=[w\hat{}(1), w\hat{}(2), \ldots, w\hat{}(N_w)]$ of the error path from the controlling speaker 105 to the error microphone 106 to the $x(t)=[x(t), x(t-1), \ldots, x(t-N_w+1)]$ obtained by expressing the reference signal x(t) by vector by the following equation (1).

$$r(t)=w\hat{}*x(t) \qquad (1)$$

(* indicates a convolution arithmetic.)

The LMS arithmetic unit 104 holds the input reference signals r(t) input from the FIR filter 103 both at the current time and in the past for the number $(N_h)$ of the taps of the FIR filter 102. Then, the coefficient $h(t+1)=[h(1, t+1), h(2, t+1), \ldots, h(N_h, t+1)]$ of the FIR filter 102 at the next time point is obtained by the following equation (2) using $r(t)=[r(t), r(t-1), \ldots, r(t-N_h+1)]$ obtained by expressing the filter reference signal by vector, and the coefficient $h(t)=[h(1, t), h(2, t), \ldots, h(N_h, t)]$ of the FIR filter 102 at the current time $$h(t+1)=h(t)+\mu\cdot e(t)\cdot r(t) \qquad (2)$$

However, e(t) is a remaining noise signal detected by the error microphone 106 at the time t, and μ indicates a step size parameter.

As illustrated in FIG. 11, and as compared with an LMS algorithm, a Filtered-X LMS algorithm is obtained by adding the FIR filter 103 with a fixed coefficient at the stage before the LMS arithmetic unit 104 in the adaptive filter 107. The basic principle of the algorithm is to update (determine) the filter coefficient of the FIR filter 102 in the steepest descent method to decrease remaining noise by considering the transfer function from the controlling speaker 105 to the error microphone 106.

The Filtered-X LMS algorithm is described in, for example, the non-patent document 1.

Generally, in an adaptive algorithm for a time area such as the Filtered-X LMS algorithm etc., an amount of silenced noise is larger in a frequency band at a higher sound pressure level. Accordingly, there is the problem that an effective silencing effect cannot be obtained when there is disagreeable noise for humans in a frequency band at a low sound pressure level.

To solve the problem, in the patent document 2, the reference signal x from a sensor microphone 111 is divided into a plurality of bands $x_1, x_2, \ldots, x_n$, through a band division unit 112 as illustrated in FIG. 12, and the remaining noise signal e from an error microphone 116 is divided into a plurality of bands $e_1, e_2, \ldots, e_n$, through a band division unit 114. In an adaptive filter unit 113 having a plurality of adaptive filters, a filter coefficient is updated (determined) for each band and a control signal to be output to a controlling speaker 115 is generated. Thus, a high silencing effect is obtained in a wide frequency band.

However, in the active silencer, a sufficient amount of silenced noise may not be acquired at some frequencies due to the aging of a controlling speaker and a microphone, the fluctuation of the spatial transmission system of an error path from a controlling speaker to an error microphone, disturbance noise mixed into the active silencer, etc.

In this case, there is a larger difference between a sound pressure level of a frequency band at which a sufficient amount of silenced noise can be obtained and a sound pressure level of a frequency band at which a sufficient amount of silenced noise can be obtained. As a result, as illustrated in FIG. 13, there can be the problem that a sound pressure level in each frequency band that is initially flat becomes partially outstanding as a non-silenced band after the sufficient lapse of time when the active silencer operates, thereby generating noisy sound with an outstanding non-silenced band.

In addition, when a filter coefficient is updated (determined) independently for each divided band (for example, in the case in FIG. 12), there occurs a more obvious problem in which it sounds exceedingly noisy in a non-silenced band.

Patent Document 1: Japanese Patent Publication No. 2872545 “Active Silencer”

Patent Document 2: Japanese Patent Publication No. 2517150 “Active Silencer”

Non-patent Document 1: B. Widrow and S. Stearns, “Adaptive Signal Processing”, Prentice-Hall, Englewood, Cliffs, N.J., 1985

SUMMARY

The present invention aims at providing an active silencer capable of avoiding outstanding noise caused by a non-silenced band, and a method for controlling the active silencer.

The active silencer according to a first aspect of the present invention includes: a speaker to generate control sound which interferes with noise; a microphone to detect noise remaining after the interference as a remaining noise signal; a sound quality evaluation unit to evaluate the sound quality of the remaining noise and outputting a result of the sound quality evaluation; an actuation signal determination unit to determine, according to the result of the sound quality evaluation, the detection timing of the frequency component of the remaining noise signal to be used when the control sound is generated for a plurality of bands of the remaining noise, corresponding to the plurality of bands of a reference signal corresponding to the noise; and a control signal generation unit to generate and output a control signal for generation of the control sound depending on a plurality of bands of the determined remaining noise signal and a plurality of bands of the reference signal corresponding to the noise.

The detection timing of a frequency component to be used when the control sound of a speaker is generated is determined by the actuation signal determination unit depending on the result of a sound quality evaluation for each band of the remaining noise signal.

Therefore, for example, if the frequency component of the current band is excessively erased as compared with an adjacent lower frequency band, or as compared with an adjacent higher frequency band, then it is possible to prevent the difference between the sound pressure level of the remaining noise of the current band and the sound pressure level of the band of one of the adjacent bands or the bands of the adjacent bands from developing not to use the frequency component detected at the current time on the current band when a control sound is generated. Therefore, for example, it is possible to avoid a non-silenced band from becoming outstandingly noisy.

The active silencer according to the second aspect is based on the first aspect. The actuation signal determination unit includes a first band division unit to divide the remaining noise signal into a plurality of frequency bands, and a switch unit having a plurality of switches for determining whether or not the frequency component of each band of the remaining noise signal detected at the current time is to be passed through the control signal generation unit depending on the result of the sound quality evaluation. The control signal generation unit includes a second band division unit to divide the reference signal into a plurality of bands corresponding to a plurality of bands of the remaining noise, an adaptive filter unit provided with a plurality of adaptive filters having a variable filter coefficient for filtering the frequency component of the reference signal detected at the current time and generating a second control signal for each corresponding band of the remaining noise signal and the reference signal so that the frequency component which has passed through the switch can be reduced, and an adder to obtain a sum of the second control signal, generating the control signal, and outputting the signal to the speaker.

The active silencer according to the third aspect of the present invention is based on the second aspect. The sound quality evaluation unit calculates the difference in the sound pressure levels between the adjacent bands of the remaining noise signal. The actuation signal determination unit controls the switch not to pass the frequency component of the remaining noise signal of the current band when the sound pressure level of the current band is equal to or smaller than a predetermined value than the sound pressure level of a lower adjacent band, or when the sound pressure level of the current band is equal to or smaller than a predetermined value than the sound pressure level of a higher adjacent band.

The active silencer according to the fourth aspect of the present invention is based on the third aspect, and further includes a threshold change unit for changing the threshold depending on the sound pressure level for each band of the remaining noise signal.

For example, the threshold change unit changes the threshold to be used in determining a band into a smaller value if the sound pressure level of the band is equal to or larger than a predetermined value when the sound pressure level of the remaining noise is outstanding in the band, and changes the threshold to be used in determining a band into a larger value if the sound pressure level of the band is smaller than the predetermined value when the sound pressure level of the remaining noise is outstanding in the band. With the configuration, when the remaining noise easily becomes noisy, the update of a filter coefficient for each divided band can be controlled so that a discontinuous spectrum cannot occur, and when the remaining noise does not easily become noisy, the update of a filter coefficient for each divided band can be controlled so that silencing performance can be improved.

In addition, for example, the threshold change unit changes the threshold to be used in determining a band into a smaller value when the band having an outstanding sound pressure level of the remaining noise refers to high sensitivity to human ears. With the configuration, control can be performed to improve the silencing performance while suppressing the generation of noisy sound (unusual sound).

According to the present invention, outstanding noise in a non-silenced band can be avoided.

DESCRIPTION OF EMBODIMENT

The embodiments of the present invention are described below in detail with reference to the attached drawings.

Figure 1:
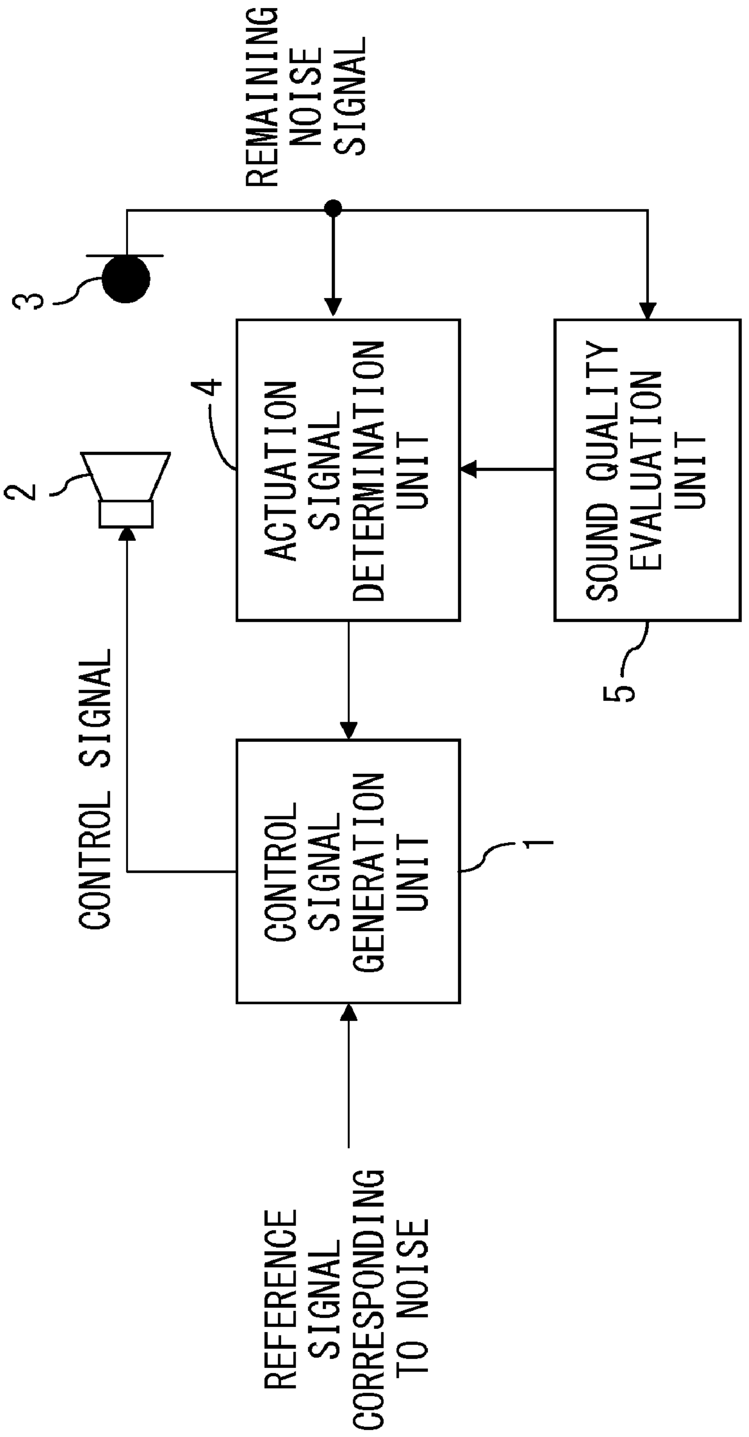
FIG. 1 is a configuration according to the principle of the active silencer of the present invention.

FIG. 1 is a configuration according to the principle of the active silencer of the present invention.

As illustrated in FIG. 1, the active silencer is configured by a controlling speaker 2, an error microphone 3, a sound quality evaluation unit 5, an actuation signal determination unit 4, and a control signal generation unit 1.

The controlling speaker 2 and the controlling speaker 2 are provided near an area on which the silencer is to work. The controlling speaker 2 generates control sound which interferes with noise. The error microphone 3 detects the noise remaining after the interference.

The sound quality evaluation unit 5 extracts the sound quality of the remaining noise and outputs a result of a sound quality evaluation. The actuation signal determination unit 4 determines the detection timing of the frequency component of the remaining noise signal to be used in generating the control sound for a plurality of bands of the remaining noise corresponding to the plurality of bands of the reference signal corresponding to the noise depending on the result of the sound quality evaluation.

The control signal generation unit 1 generates and outputs a control signal for generation of the control sound on the basis of the plurality of bands of the determined remaining noise signal, and the plurality of bands of the reference signal corresponding to the noise.

Figure 2:
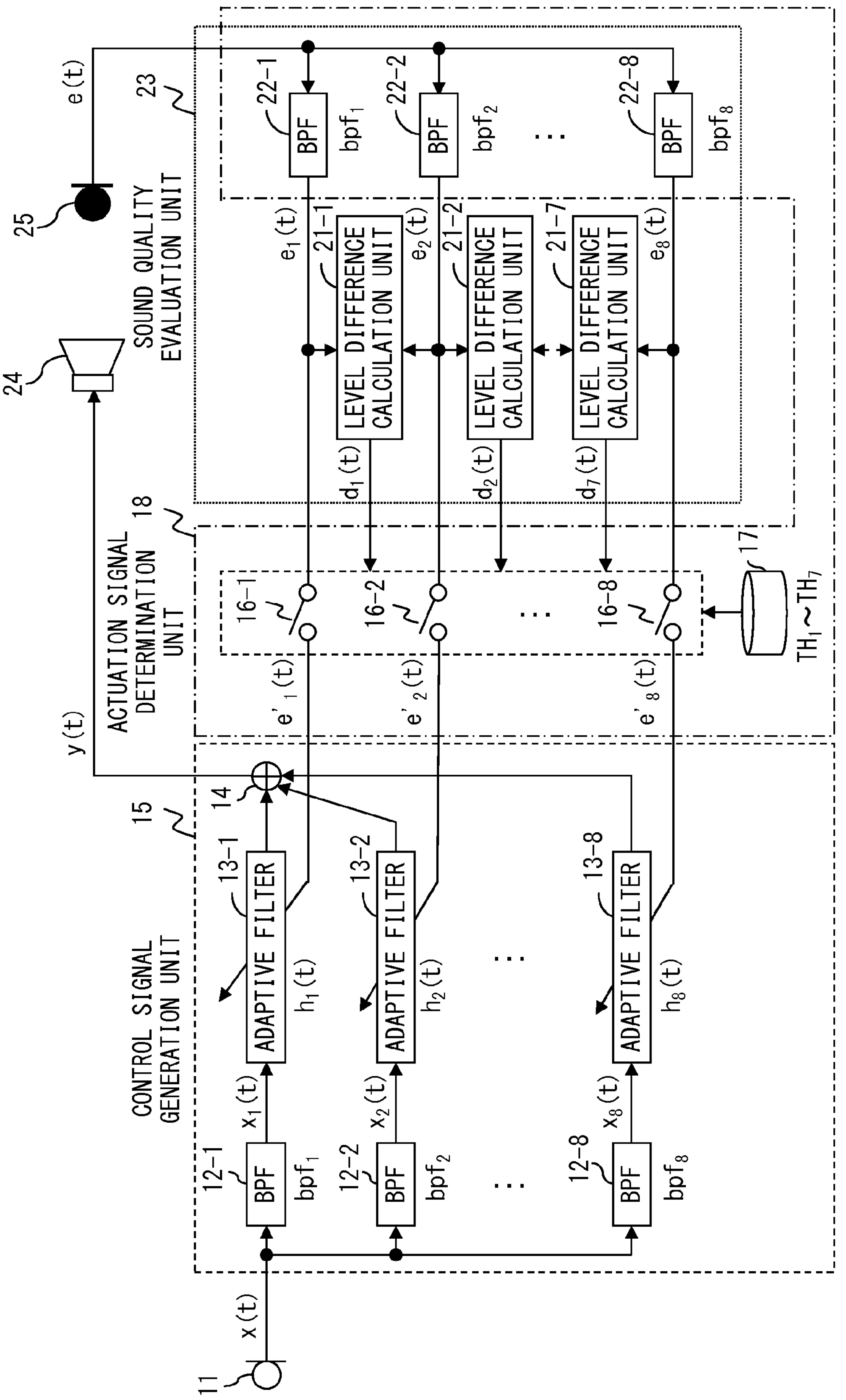
FIG. 2 is a configuration of the active silencer according to the first embodiment of the present invention.

FIG. 2 is a configuration of the active silencer according to the first embodiment of the present invention.

As illustrated in FIG. 2, the active silencer according to the first embodiment is configured by a sensor microphone 11, a control signal generation unit 15, a controlling speaker 24, an actuation signal determination unit 18, an error microphone 25, and a sound quality evaluation unit 23.

The sensor microphone 11 detects a reference signal corresponding to noise.

The control signal generation unit 15 is provided with: a band division unit configured by eight band pass filters (hereinafter referred to as a BPF), that is, BPFs 12-1, 12-2, . . . , and 12-8, for dividing a signal corresponding to the noise detected by the sensor microphone 11 into eight predetermined bands; an adaptive filter unit configured by eight adaptive filters, that is, adaptive filters 13-1, 13-2, . . . , and 13-8, for filtering each of the divided bands; and an adder 14 for adding up the output of the respective adaptive filters.

The error microphone 25 detects remaining noise remaining after the control sound emitted by the controlling speaker 24 interferes with noise.

The sound quality evaluation unit 23 is provided with: a band division unit configured by eight band pass filters, that is, BPFs 22-1, 22-2, . . . , and 22-8, for dividing a remaining noise signal detected by the error microphone 25 into eight predetermined bands; and an inter-adjacent-band level difference calculation unit (of a remaining noise signal) configured by a level difference calculation unit 21-1 for calculating a level difference between output of the BPF 22-1 and output of the BPF 22-2; a level difference calculation unit 21-2 for calculating a level difference between output of the BPF 22-2 and output of the BPF 22-3; . . . ; and a level difference calculation unit 21-7 for calculating a level difference between output of the BPF 22-7 and output of the BPF 22-8.

It is obvious that the bands passed by the BPFs 12-1, 12-2, . . . , and 12-8 match the bands passed respectively by the BPFs 22-1, 22-2, . . . , and 22-8.

The actuation signal determination unit 18 is provided with: a band division unit configured by the above-mentioned BPFs 22-1, 22-2, . . . , and 22-8; and a switch unit having a plurality of switches 16-1, 16-2, . . . , and 16-8 for comparing the calculated sound pressure level difference between the bands with a corresponding threshold in a plurality of thresholds $TH_1$ through $TH_7$ stored in a threshold storage unit 17, and determining whether or not the output of the BPFs 22-1, 22-2, . . . , and 22-8 is to be transmitted to the adaptive filters 13-1, 13-2, . . . , and 13-8 at the current time.

Then, the operation of the active silencer according to the first embodiment is described below with reference to the configuration in FIG. 2 and the flowchart in FIG. 3.

The active silencer in FIG. 2 performs in parallel the operation by the control signal generation unit 15 for processing a reference signal corresponding to the noise detected by the sensor microphone 11 and the operation of the sound quality evaluation unit 23 and the actuation signal determination unit 18 for processing the remaining noise signal detected by the error microphone 25. However, in the adaptive filters 13-1, 13-2, . . . , and 13-8, when the filter coefficients $h_1(t)$, $h_2(t)$, . . . , $h_8(t)$ are updated, the frequency components corresponding to the reference signal and the remaining noise signal detected at the same time are used in an arithmetic operation.

Figure 3:
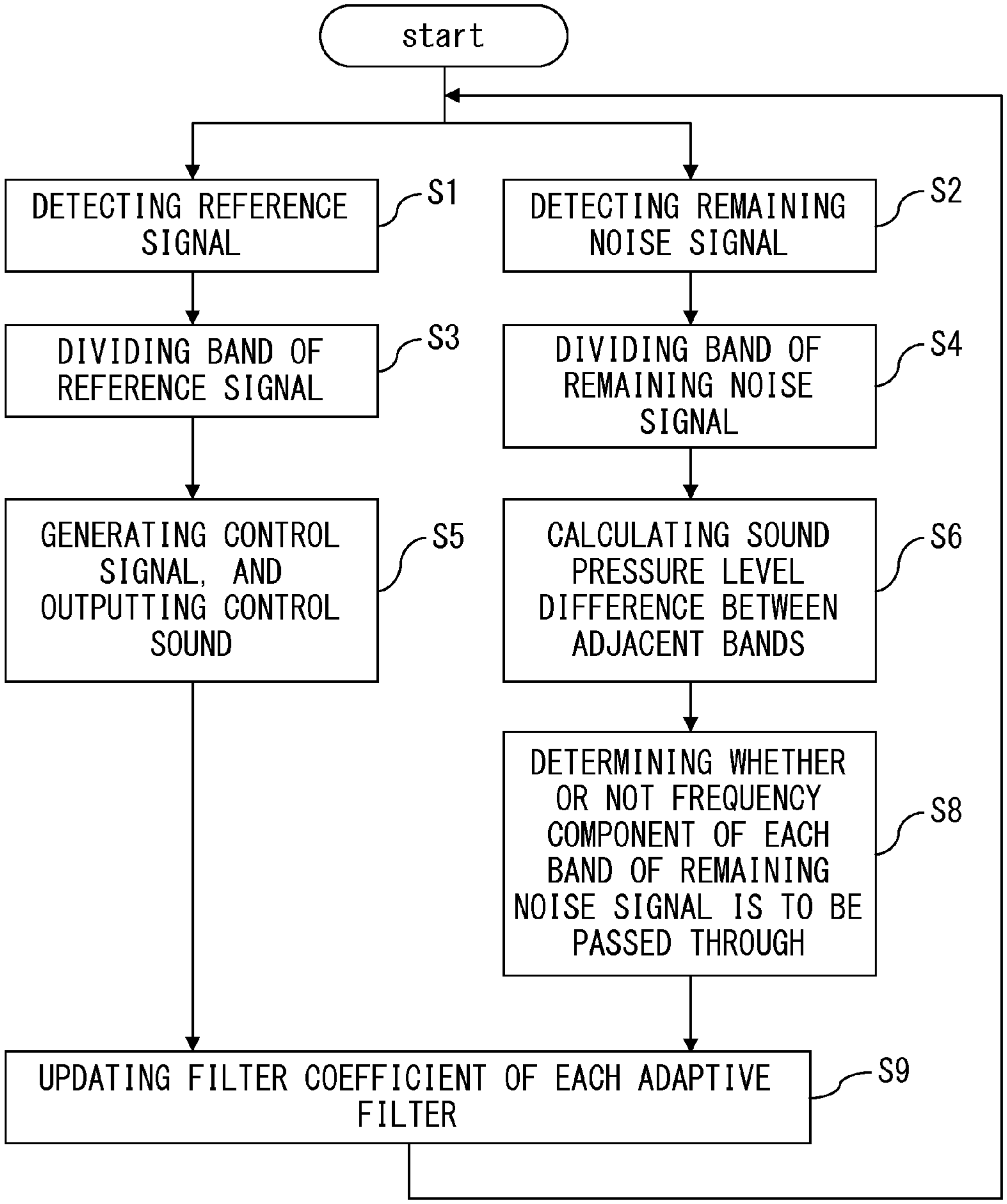
FIG. 3 is a flowchart of the operation of the active silencer according to the first embodiment of the present invention.

The above-mentioned process is illustrated in the flowchart in FIG. 3 by the meeting in step S9 of the flow of steps S1→S3→S5→S9 and the flow of steps S2→S4→S6→S8→S9.

In step S1 in FIG. 3, the sensor microphone 11 detects a reference signal x(t). In step S3, the detected reference signal x(t) is input to the band pass filters (BPF) 12-1, 12-2, . . . , and 12-8, and the band is divided into eight sections. Then, as a result of the division, an update signal $x_i(t)$ (i=1, 2, . . . , 8) is obtained by each BPF by the following equation (3), and output to the adaptive filters 13-1, 13-2, . . . , and 13-8 at the subsequent stage.

$$x_i(t)=bpf_i*x(t)\ (i=1, 2, \ldots, 8) \tag{3}$$

Figure 4:
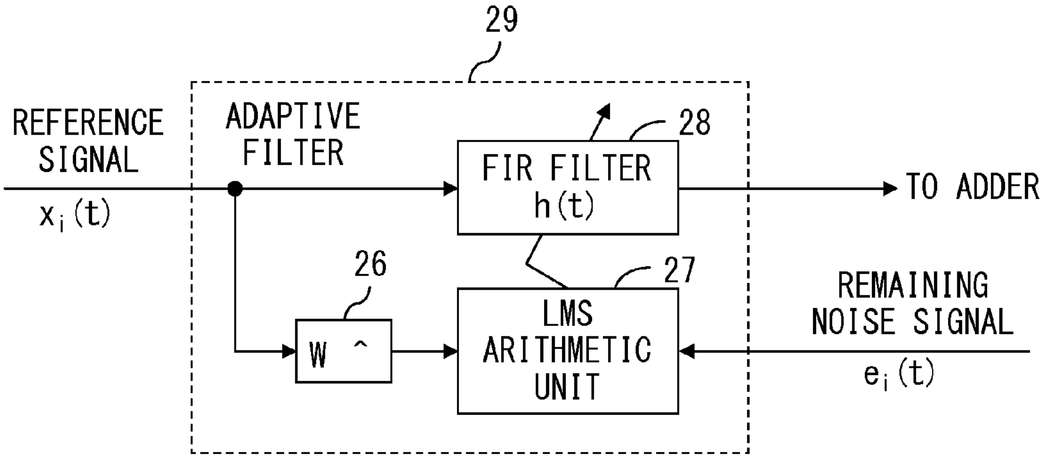
FIG. 4 illustrates the detailed configuration of each adaptive filter illustrated in FIG. 2.

FIG. 4 illustrates the detailed configuration of each adaptive filter illustrated in FIG. 2.

As illustrated in FIG. 4, an adaptive filter 29 is configured by an LMS arithmetic unit 27 for performing an arithmetic operation on the basis of the LMS algorithm, a FIR filter 26 provided at the stage preceding the LMS arithmetic unit 27 and having a fixed filter coefficient, and a FIR filter 28 for which a variable filter coefficient can be set.

The number of taps of the FIR filters 26 is $N_w$, and is assigned by the transfer function w^=[w^(1), w^(2), . . . , w^($N_w$)] of the error path from the controlling speaker 24 to the error microphone 25. In addition, the FIR filter 26 holds $x_i(t)=[x_i(t), x_i(t-1), \ldots, x_i(t-N_w+1)]$ obtained by sampling $N_w$ reference signals $x_i(t)$ at the current time and each time point in the past, and outputs the convolution signal (filter reference signal) by the following equation (4) to the LMS arithmetic unit 27

$$r_i(t)=\hat{w}*x_i(t) \tag{4}$$

(* indicates a convolution arithmetic.)

The number of taps of the LMS arithmetic unit 27 is $N_h$, and the unit holds $r_i(t)=[r_i(t), (t-1), \ldots, r_i(t-N_h+1)]$ obtained by sampling $N_h$ filter reference signals at the current time and each time point in the past, obtains the filter coefficient $h_i(t+1)=[h_i(1, t+1), h_i(2, t+1), \ldots, h_i(N_h, t+1)]$ at the next time point (t+1) from the filter coefficient $h_i(t)=[h_i(1, t), h_i(2, t), \ldots, h_i(N_h, t)]$ at tie time t by the following equation (5), and outputs the result to the FIR filter 28.

$$h_1(t+1)=h_i(t)+\mu\cdot e_i(t)\cdot r_i(t) \tag{5}$$

where $e_i(t)$ indicates the i-th frequency component of the band-divided remaining noise signal detected by the error microphone 106 at the time t, and μ indicates a step size parameter.

The number of taps of the FIR filter 28 is $N_h$, and the filter holds $x_i(t)=[x_i(t), x_i(t-1), \ldots, x_i(t-N_h+1)]$ obtained by sampling $N_h$ reference signals $x_i(t)$ at the current time and each time point in the past, multiplies the $x_i(t)$ by the filter coefficient $h_i(t)=[h_i(1, t), h_i(2, t), \ldots, h_i(N_h, t)]$ at the current time, and outputs a result of the multiplication to the adder 14 illustrated in FIG. 2.

Upon receipt of the output of each adaptive filter, the adder 14 obtains a sum by the following equation (6), and outputs the sum as a control signal to the controlling speaker 24.

$$y(t)=\sum_{i=1}^{8} h_i^{\rightarrow}(t)*x_i^{\rightarrow}(t) \quad (6)$$

Back to FIG. 3, a control signal is generated in step S5 after step S3 by the adaptive filters 13-1, 13-2, . . . , and 13-8 and the adder 14 as described with reference to FIG. 4 above, and output to the controlling speaker 24. The controlling speaker 24 generates control sound on the basis of the control signal. Then, control is passed to step S9.

As another flow illustrated in FIG. 3, the remaining noise signal e(t) is detected by the error microphone 25 in step S2.

In step S4, the detected remaining noise signal e(t) is input to the band pass filters (BPF) 22-1, 22-2, . . . , and 22-8, and the band is divided into eight sections. Then, the signal $e_i(t)$ (i=1, 2, . . . , 8) as a result of the division is obtained by each BPF by the following equation (7), and output to the level difference calculation units 21-1, 21-2, . . . , and 21-7 and the switches 16-1, 16-2, . . . , and 16-8 at the subsequent stages.

$$e_i(t)=bpf_i*e(t)\ (i=1, 2, \ldots, 8) \quad (7)$$

Figure 5:
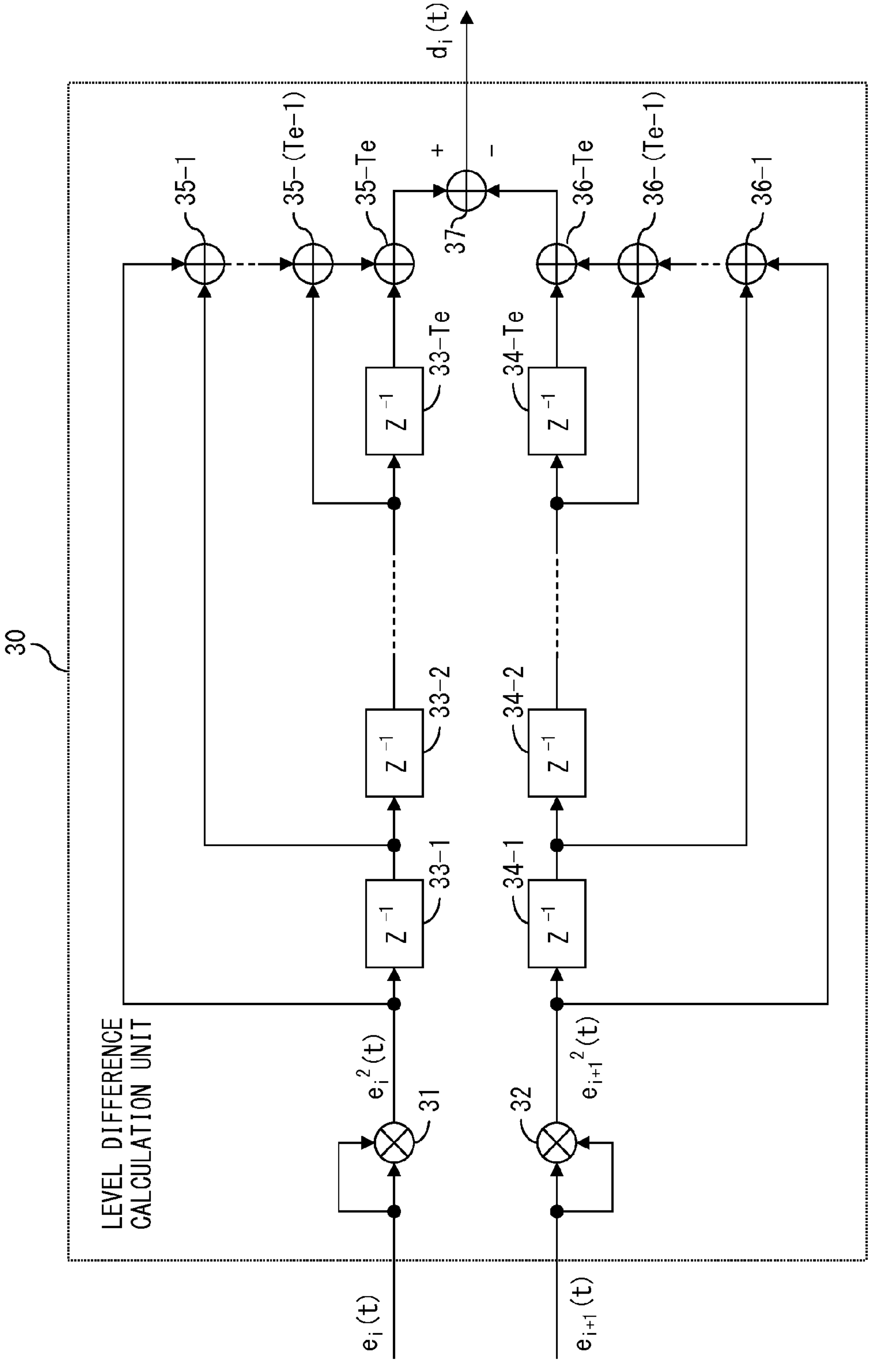
FIG. 5 illustrates the detailed configuration of each level difference calculation unit illustrated in FIG. 2.

FIG. 5 illustrates the detailed configuration of each level difference calculation unit illustrated in FIG. 2.

In FIG. 5, a level difference calculation unit 30 averages and calculates the level differences of the frequency components $e_i(t)$ and $e_{i+1}(t)$ (i=1, . . . , 7) between two adjacent bands obtained by band-dividing the remaining noise signal e(t) for the period Te hours back from the current time up to now.

A multiplexer 31 calculates the square of $e_i(t)(\{e_i(t)\}^2)$ from $e_i(t)$. Delay units 33-1, 33-2, . . . , and 33-Te respectively latch the value at the current time and at each time in the past, that is, $\{e_i(t)\}^2$, $\{e_i(t-1)\}^2$, . . . , $\{e_i(t-Te)\}^2$. An adder 35-1 adds $\{e_i(t)\}^2$ and $\{e_i(t-1)\}^2$, . . . , an adder 35-(Te-1) adds a result of the addition of an adder 35-(Te−2) to $\{e_i(t-Te+1)\}^2$, and an adder 35-Te adds a result of the addition of the adder 35-(Te−1) to $\{e_i(t-Te)\}^2$.

A multiplexer 32 calculates the square of $e_{i+1}(t)$ ($\{e_{i+1}(t)\}^2$) from $e_{i+1}(t)$. Delay units 34-1, 34-2, . . . , and 34-Te respectively latch the value at the current time and at each time in the past, that is, $\{e_{i+1}(t)\}^2$, $\{e_{i+1}(t-1)\}^2$, . . . , $\{e_{i+1}(t-Te)\}^2$. An adder 36-1 adds $\{e_{i+1}(t)\}^2$ and $\{e_{i+1}(t-1)\}^2$, . . . , an adder 36-(Te−1) adds a result of the addition of an adder 36-(Te−2) to $\{e_{i+1}(t-Te+1)\}^2$, and an adder 36-Te adds a result of the addition of the adder 36-(Te−1) to $\{e_{i+1}(t-Te)\}^2$.

An adder 37 subtracts the output of the adder 36-Te from the output of the adder 35-Te. The output of the adder 37 is assigned by the following equation (8).

$$d_i(t)=\sum_{j=0}^{Te}\{e_i(t-j)\}^2-\sum_{j=0}^{Te}\{e_{i+1}(t-j)\}^2 \quad (8)$$

In step S6 after step S4 back in FIG. 3, the (sound pressure) level difference between the adjacent bands of the remaining noise signal is calculated as described above with reference to FIG. 5.

In step S8, it is determined whether or not the frequency component is to be passed through each of the bands of the remaining noise signal depending on whether or not the switches 16-1, 16-2, . . . , and 16-8 are to be conducting.

Figure 6A:
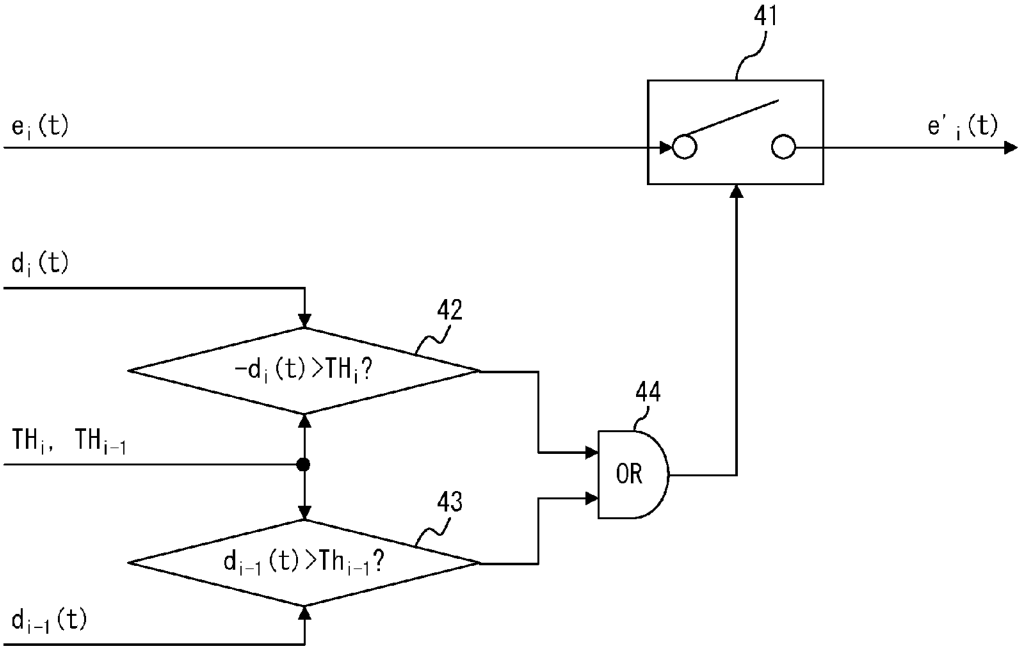
FIG. 6A illustrates the detailed configuration of any of the switches 16-2, . . . , and 16-7.

FIG. 6A illustrates the detailed configuration of any of the switches 16-2, . . . , and 16-7 in FIG. 2.

In FIG. 6A, a switch 41 determines whether or not the remaining noise signal $e_i(t)$ (i=2, . . . , 7) is to be conducting depending on the output of an OR arithmetic unit 44.

A determination unit 42 determines whether or not $-d_i(t)$ obtained by inverting the sign of the sound pressure level difference $d_i(t)$ is larger than the threshold $TH_i$, and a determination unit 43 determines whether or not the sound pressure level difference $d_{i-1}(t)$ is larger than the threshold $TH_{i-1}$.

The OR arithmetic unit 44 outputs a signal for disabling the switch 41 to be conducting when the determination unit 42 issues a signal indicating that $-d_i(t)$ is larger than the threshold $TH_1$, or the determination unit 43 issues a signal indicating that $-d_{i-1}(t)$ is larger than the threshold $TH_{i-1}$.

Figure 6B:
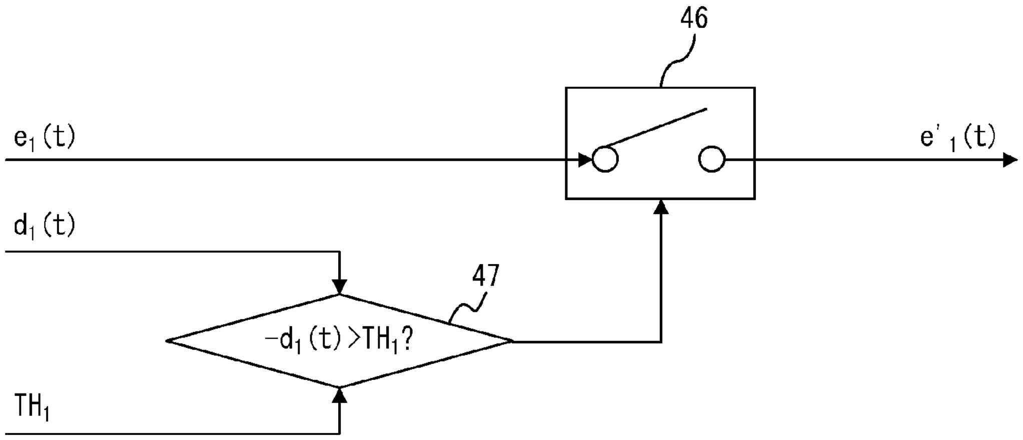
FIG. 6B illustrates the detailed configuration of the switch 16-1 illustrated in FIG. 2.

FIG. 6B illustrates the detailed configuration of the switch 16-1 illustrated in FIG. 2.

In FIG. 6B, a switch 46 determines whether or not the remaining noise signal $e_1(t)$ is to be conducting depending on the output of a determination unit 47.

The determination unit 47 determines whether or not $-d_1(t)$ obtained by inverting the sign of the sound pressure level difference $d_1(t)$ is larger than the threshold $TH_1$. If it is determined that $-d_1(t)$ is larger than the threshold $TH_1$, it outputs a signal for disabling the switch 46 to be conducting.

Figure 6C:
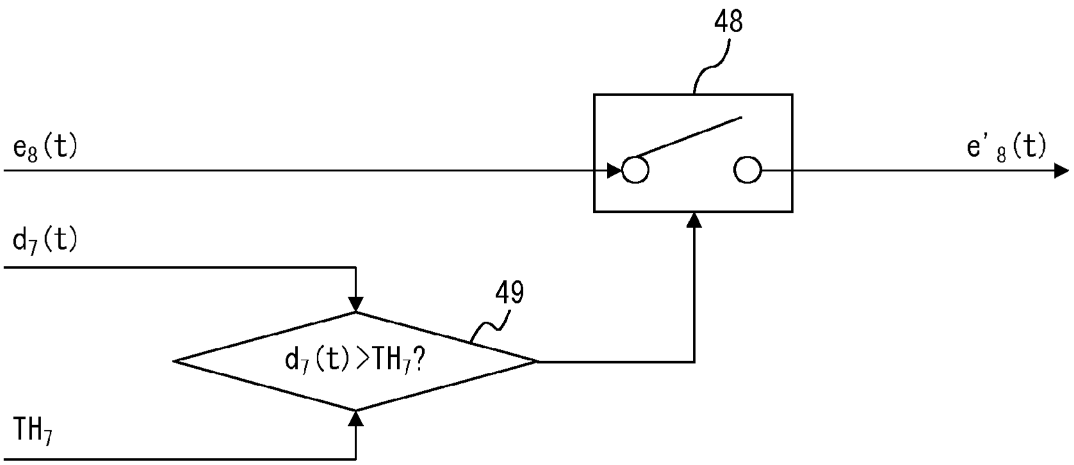
FIG. 6C illustrates the detailed configuration of the switch 16-8 illustrated in FIG. 2.

FIG. 6C illustrates the detailed configuration of the switch 16-8 illustrated in FIG. 2.

In FIG. 6C, a switch 48 determines whether or not the remaining noise signal $e_8(t)$ depending on the output of a determination unit 49.

The determination unit 49 determines whether or not the sound pressure level difference $d_7(t)$ is larger than the threshold $TH_8$. If it is determined that $d_7(t)$ is larger than the threshold $TH_7$, the unit outputs a signal for disabling the switch 48 to be conducting.

Thus, in step S8 illustrated in FIG. 3, it is determined whether or not a frequency component is to be passed through each band of a remaining noise signal by the following equations (9) through (11).

$$e_i'(t)=\begin{cases}0 & (d_{i-1}(t)>TH_{i-1}\ \text{OR}\ -d_i(t)>TH_i)\\ e_i(t) & (d_{i-1}(t)\leqq TH_{i-1}\ \text{AND}\ -d_i(t)\leqq TH_i)\end{cases} \quad (9)$$

(where $i=2, \ldots, 7$)

$$e_l'(t)=\begin{cases}0 & (-d_1(t)>TH_1)\\ e_1(t) & (-d_1(t)\leqq TH_1)\end{cases} \quad (10)$$

$$e_8'(t)=\begin{cases}0 & (d_7(t)>TH_7)\\ e_8(t) & (d_7(t)\leqq TH_7)\end{cases} \quad (11)$$

In step S9 illustrated in FIG. 3, the filter coefficient $h_{i+1}(t)$ of each adaptive filter at the next time point (t+1) is obtained by the equation (5) described above with reference to FIG. 4 on the basis of the frequency component $x_i(t)$ of each band of the reference signal x(t), $e'_i(t)$ obtained from the frequency component $e_i(t)$ of each band of the remaining noise signal e(t), and the filter coefficient $h_i(t)$ of each adaptive filter at the current time t.

Figure 7:
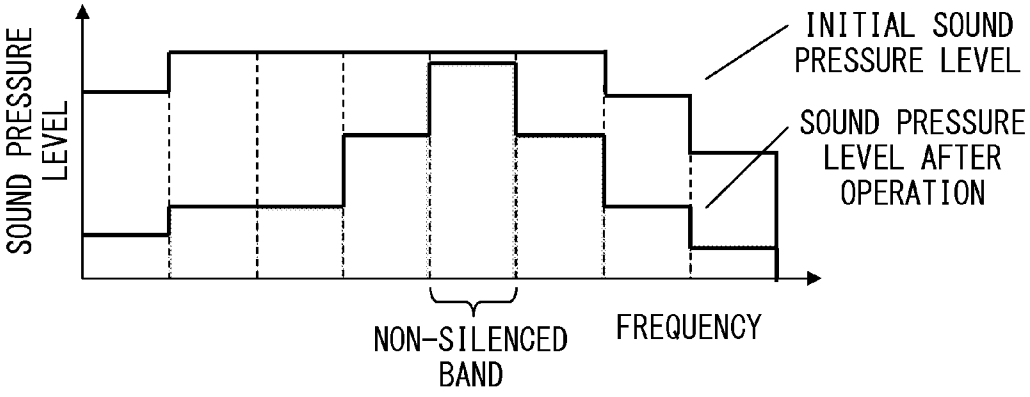
FIG. 7 illustrates the sound pressure level of each band at the initial stage, and the sound pressure level of each band after the activation of the active silencer according to the present invention.

FIG. 7 illustrates the sound pressure level of each band at the initial stage, and the sound pressure level of each band after the activation of the active silencer according to the present invention.

FIG. 7 illustrates, for example, the sound pressure level of the bands passed through by the BPFs 22-1, 22-2, . . . , and 22-8 in order from the rightmost. In this example, the sound pressure level of the band passed through by the BPF 22-5 is outstanding, and the band corresponds to the non-silenced band.

The sound pressure level of each frequency band of the remaining noise is initially flat, and after some time has passed with the active silencer according to the first embodiment operated, the occurs differences in silencing performance among the bands.

However, in the first embodiment, the actuation signal determination unit 18 determines whether or not the frequency component $e_i(t)$ (i=1, . . . , 8) detected at the current time t is to be passed through the i-th adaptive filter 13-*i* for each frequency band of remaining noise.

As illustrated in FIGS. 6A through 6C, if the frequency component of the current band is excessively erased (exceeding the threshold) as compared with an adjacent lower frequency band, or excessively erased (exceeding the threshold) as compared with an adjacent higher frequency band for the current band during the determination, then the frequency component detected at the current time is prevented from being output to the adaptive filter on the current band.

In this case, the filter coefficient of the adaptive filter corresponding to the current band is not updated from the time point when the threshold is exceeded, and the frequency component of the current band is no more erased according to the remaining noise signal. Therefore, each band can be silenced while preventing the development of the difference between the sound pressure level of the remaining noise of the current band and the sound pressure level of the band of one of the adjacent bands or the sound pressure levels of both of the adjacent bands, thereby protecting the non-silenced band from sounding noisy.

In FIG. 7, a non-silenced band is included in the bands to be passed through one BPF. However, even when a non-silenced band spans a plurality of bands to be passed through a plurality of BPFs, the method by the equations (9) through (11) according to the first embodiment is effective.

Described below is the second embodiment.

The configurations of the devices are different in the spectrum continuity evaluating portion of remaining noise between the first and second embodiments.

In the first embodiment, remaining noise is divided into a plurality of bands using a plurality of band pass filters, and the sound pressure level difference between adjacent bands are calculated. On the other hand, in the second embodiment, the frequency of remaining noise is analyzed, and the sound pressure level difference between the bands is calculated using the power spectrum calculated on the basis of the result of the frequency analysis.

Figure 8:
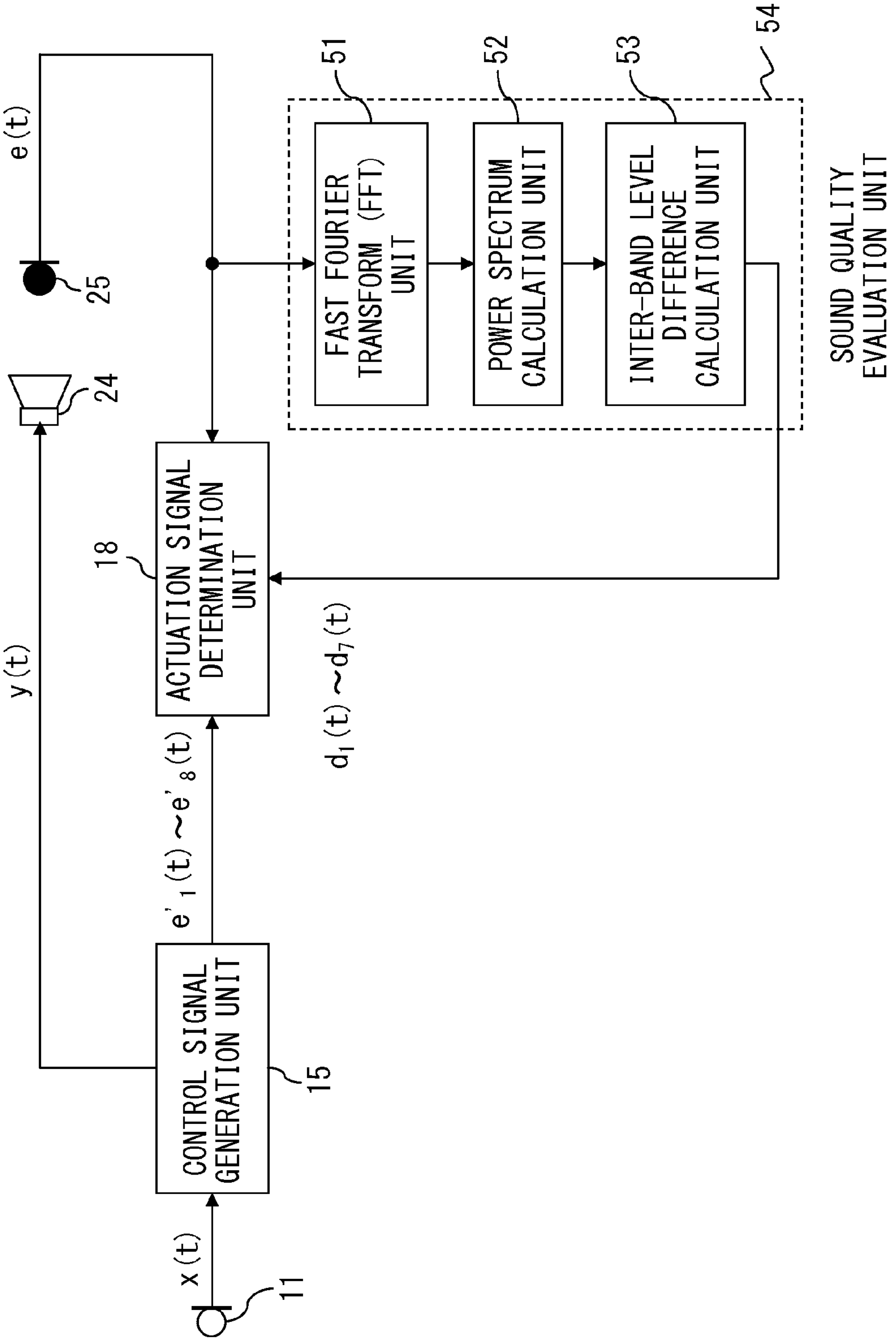
FIG. 8 is a configuration of the active silencer according to the second embodiment of the present invention.

FIG. 8 is a configuration of the active silencer according to the second embodiment of the present invention.

In FIG. 8, the components are the same as those illustrated in FIG. 2 except a sound quality evaluation unit 54, and the descriptions of these components are omitted here.

The sound quality evaluation unit 54 includes a fast Fourier transform processing unit (FFT processing unit) 51, a power spectrum calculation unit 52, and an inter-band level difference calculation unit 53.

The fast Fourier transform processing unit 51 analyzes the frequency of the remaining noise signal e(t) from the error microphone 25.

The power spectrum calculation unit 52 calculates the power spectrum on the basis of the result obtained by the frequency analysis.

The inter-band level difference calculation unit 53 calculates the difference of the sound pressure level between the adjacent bands in a plurality of bands passed by a plurality of BPSs provided in the actuation signal determination unit 18 on the basis of the calculated power spectrum.

The calculated level differences $d_1(t)$ to $d_7(t)$ between the adjacent bands are output to the actuation signal determination unit 18. The subsequent operations are the same as those according to the first embodiment.

Described next is the third embodiment.

Figure 9:
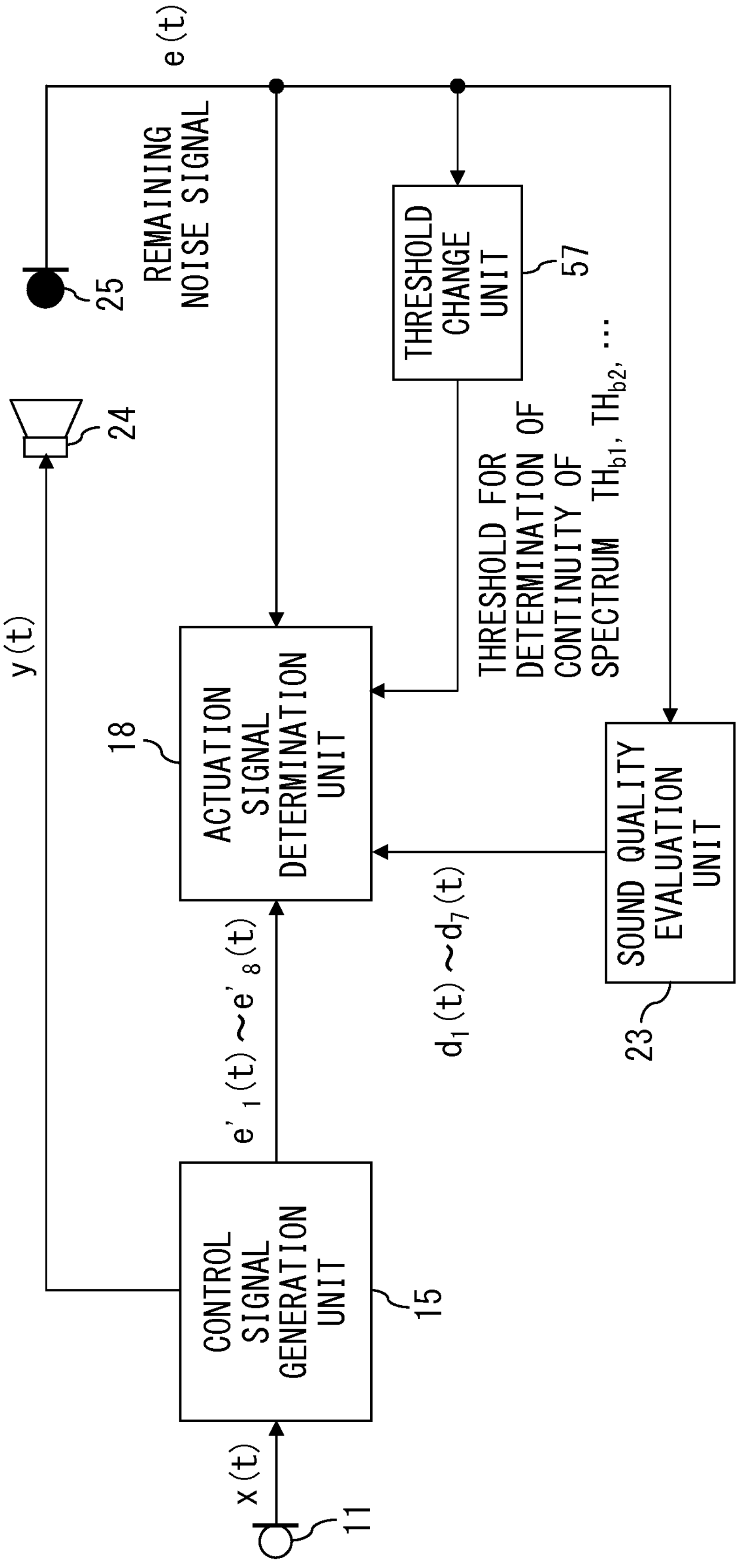
FIG. 9 is a configuration of the active silencer according to the third embodiment of the present invention.

FIG. 9 is a configuration of the active silencer according to the third embodiment of the present invention.

In FIG. 9, a threshold change unit 57 for dynamically changing a threshold for determination of the continuous spectrum of remaining noise is added to the configuration illustrated in FIG. 2.

Figure 10:
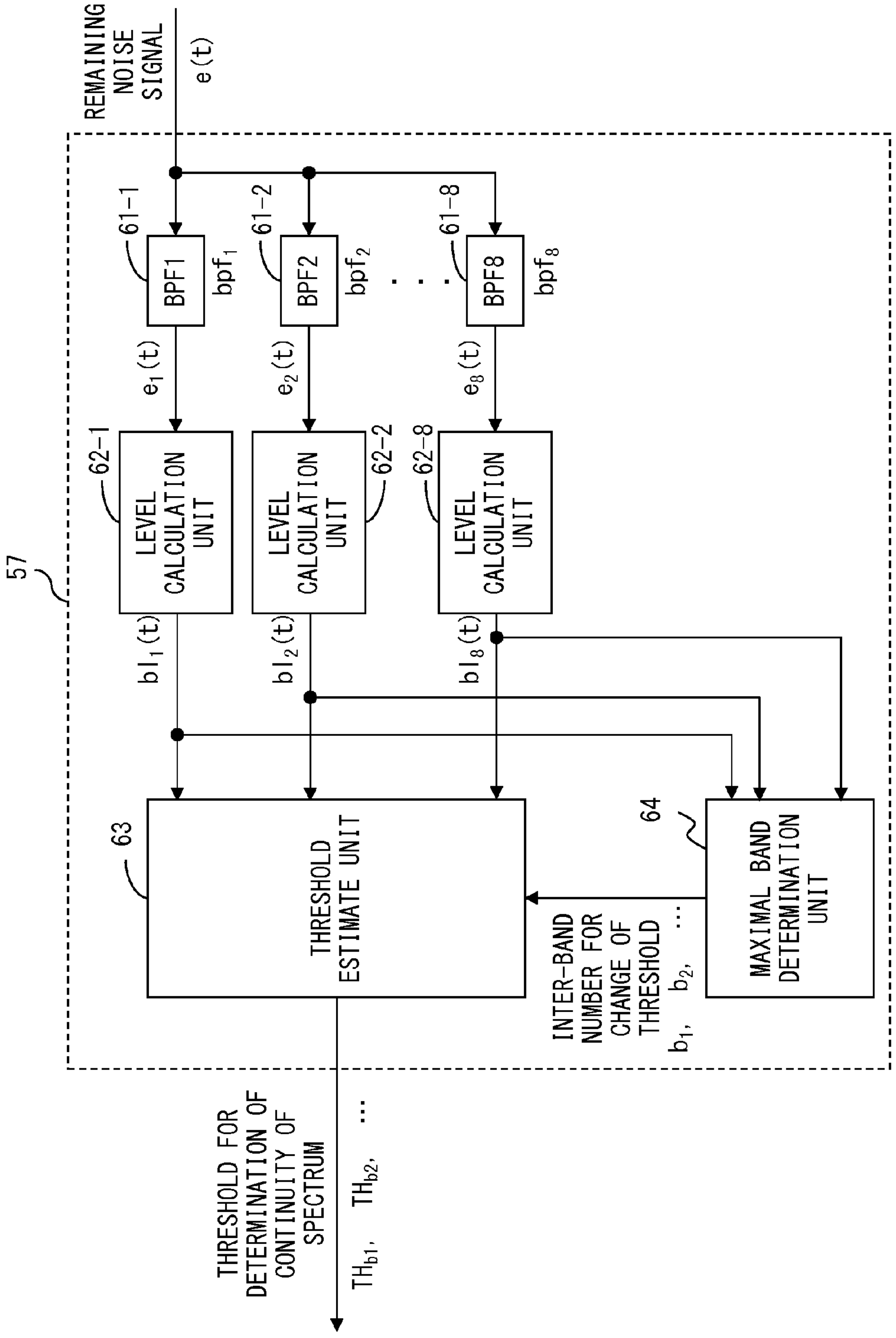
FIG. 10 illustrates the detailed configuration of the threshold change unit in FIG. 9.
Figure 11:
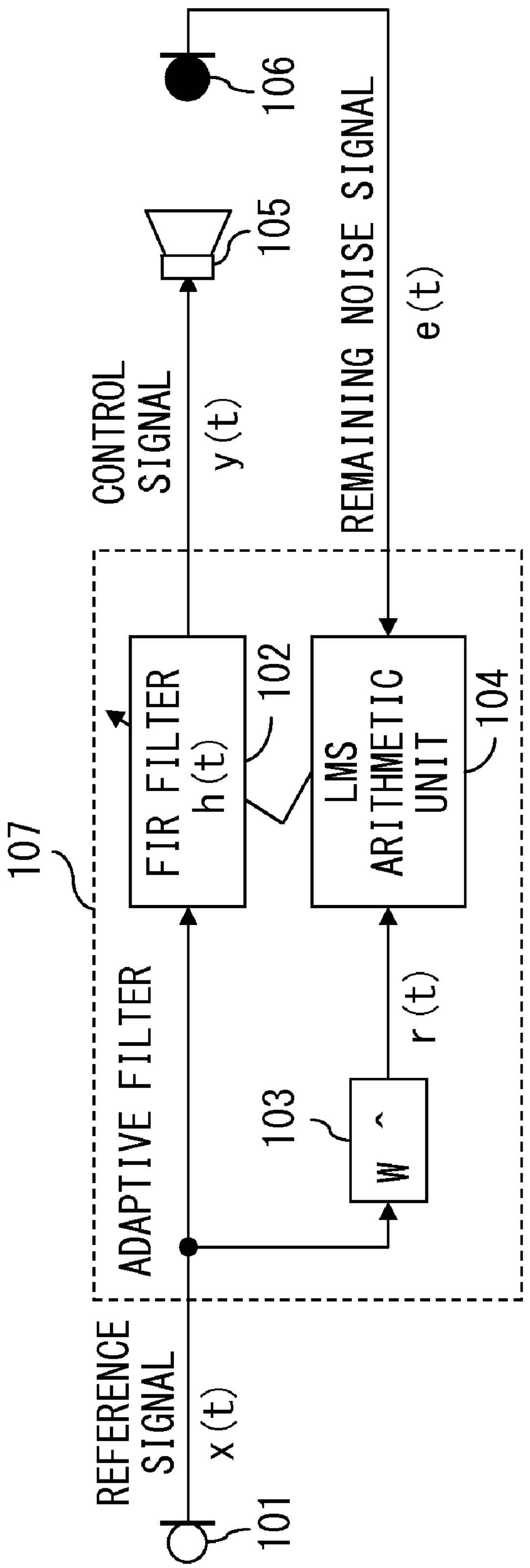
FIG. 11 is a configuration of the active silencer according to the first prior art.
Figure 12:
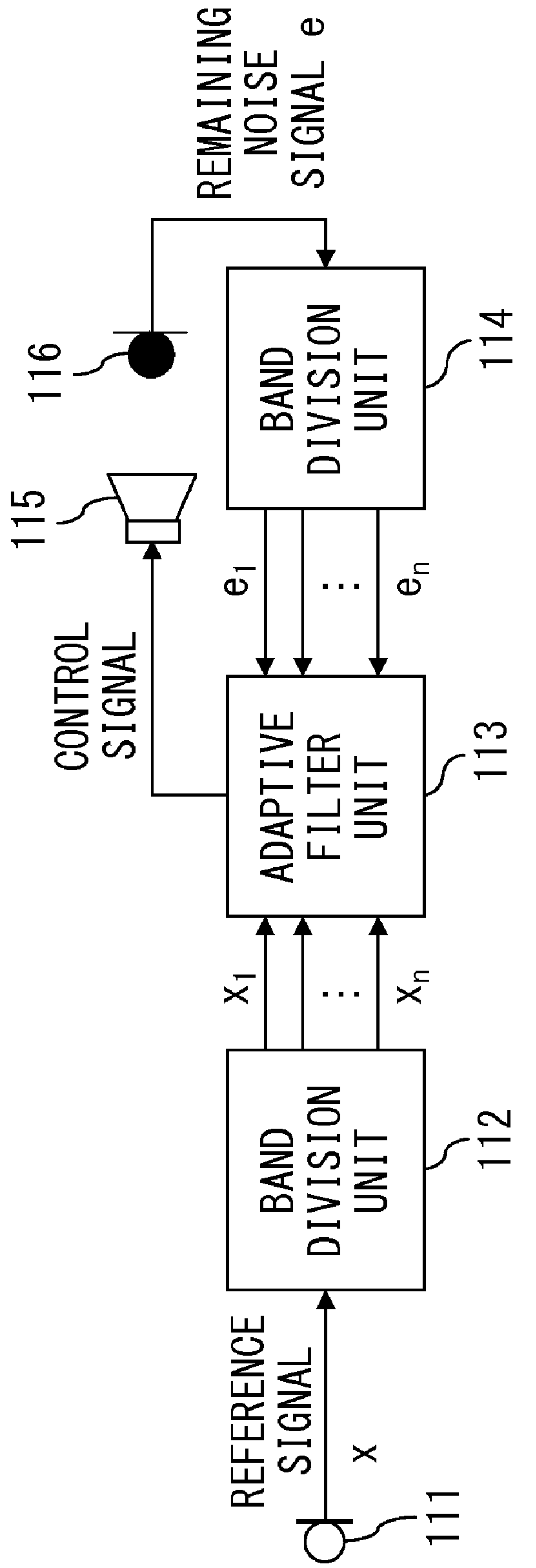
FIG. 12 is a configuration of the active silencer according to the second prior art.
Figure 13:
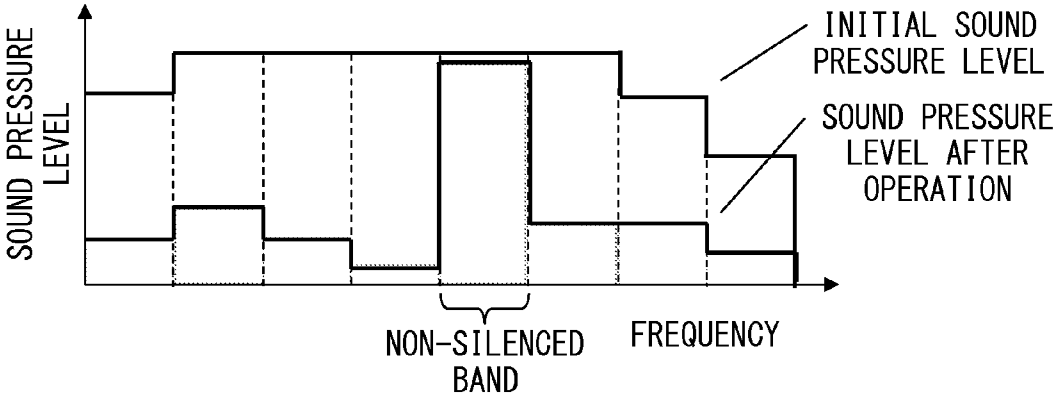
FIG. 13 illustrates the sound pressure level of each band at the initial stage, and the sound pressure level of each band after the activation of the active silencer according to the prior art.

FIG. 10 illustrates the detailed configuration of the threshold change unit in FIG. 9.

In FIG. 10, the threshold change unit 57 is configured by BPF 61-1, . . . , and BPF 61-8, level calculation units 62-1, . . . , and level difference calculation unit 62-8, a maximal band determination unit 64, and a threshold estimate unit 63.

The BPF 61-1, . . . , and BPF 61-8 divide the remaining noise signal e (t) from the error microphone 25 into eight bands corresponding to the eight BPFs of the actuation signal determination unit 56.

The level calculation units 62-1, . . . , and level difference calculation unit 62-8 respectively input the band components $e_1(t), \ldots, e_8(t)$ of the remaining noise signal, and calculate the average value of the band components for Te hours, thereby obtaining the average value of the sound pressure level of each band.

A level calculation unit **62*i*** for processing the i-th (i=1, . . . , 8) band component $e_i$ (t) performs, for example, the following operation.

The square of $e_i(t)$ ($\{e_i(t)\}^2$) is calculated from the input $e_i(t)$. In addition, by obtaining the sum of the values at the respective time points at the current time and in the past, that is, $\{e_i(t)\}^2, \{e_i(t-1)\}^2, \ldots, \{e_i(t-Te)\}^2$ latched in a plurality of delay units (not illustrated in the attached drawings), the output $Bl_i$ of the level calculation unit 62-1 can be obtained by the following equation (12).

$$bl_1(t) = \sum_{j=0}^{Te} \{e_i(t-j)\}^2 \tag{12}$$

The maximal band determination unit 64 inputs the output $\mathbf{b1}_1$, $\mathbf{b1}_8$ of the level calculation units 62-1, . . . , and level difference calculation unit 62-8 as the sound pressure levels of the respective bands, compares the sound pressure levels of the respective bands, determines a band (maximal band) having a higher sound pressure level than the surrounding bands, and outputs the inter-band numbers b1, b2, . . . indicating both ends of the band determined as the maximal band to the threshold estimate unit 63.

The threshold estimate unit 63 changes the values of the thresholds $TH_{b1}$, $TH_{b2}$, . . . corresponding to the inter-band numbers b1, b2, . . . from the maximal band determination unit 64, and outputs the resultant values to the threshold storage unit 17 in the actuation signal determination unit 18 illustrated in FIG. 9.

Described next is two methods of changing the threshold of a specified inter-band number by the threshold estimate unit 63.

In the first method, a threshold is changed as follows.

1. Independent of a threshold among bands, a second threshold is assigned for determination as to whether or not a sound pressure level of each band is high.
2. When the sound pressure level of the maximal band of remaining noise is higher than the second threshold, a smaller value is set as a threshold among the bands (thus, when remaining noise tends to sound noisy, the update of a filter coefficient can be controlled for each divided band not to cause a discontinuous spectrum).
3. When the sound pressure level of the maximal band of remaining noise is equal to or lower than the second threshold, a larger value is set as a threshold among the bands (thus, when remaining noise tends to sound noisy, the update of a filter coefficient can be controlled for each divided band to improve the silencing performance).

By performing the above-mentioned control, the silencing performance can be enhanced without generating noisy sound (unusual sound) even when a hardly-silenced ban is changed by the ambient noise or the surrounding environment of the active silencer in the first method.

A threshold is changed as follows in the second method.

When the maximal band of remaining noise belongs to a high sensitive band for human ears, the threshold for the band is set as a smaller value. With the configuration, control can be performed to improve the silencing performance while suppressing the generation of noisy sound (unusual sound).

What is claimed is:

1. An active silencer comprising:

a speaker to generate control sound which interferes with noise;

a microphone to detect noise remaining after the interference as a remaining noise signal;

a sound quality evaluation unit to evaluate sound quality of the remaining noise and output a result of the sound quality evaluation;

an actuation signal determination unit to determine, according to the result of the sound quality evaluation, detection timing of a frequency component of a remaining noise signal to be used when the control sound is generated for a plurality of bands of the remaining noise, corresponding to the plurality of bands of a reference signal corresponding to the noise; and a control signal generation unit to generate and output a control signal for generation of the control sound depending on a plurality of bands of the determined remaining noise signal and a plurality of bands of the reference signal corresponding to the noise.

2. The active silencer according to claim 1, wherein the actuation signal determination unit comprises:

a first band division unit to divide the remaining noise signal into a plurality of frequency bands; and a switch unit having a plurality of switches for determining whether or not the frequency component of each band of the remaining noise signal detected at the current time is to be passed through the control signal generation unit depending on the result of the sound quality evaluation; and the control signal generation unit comprises:

a second band division unit to divide the reference signal into a plurality of bands corresponding to a plurality of bands of the remaining noise;

an adaptive filter unit provided with a plurality of adaptive filters having a variable filter coefficient for filtering the frequency component of the reference signal detected at the current time and generating a second control signal for each corresponding band of the remaining noise signal and the reference signal so that the frequency component which has passed through the switch can be reduced; and an adder to obtain a sum of the second control signal, generating the control signal, and outputting the signal to the speaker.

3. The active silencer according to claim 2, wherein the sound quality evaluation unit calculates the difference in the sound pressure levels between the adjacent bands of the remaining noise signal;

the actuation signal determination unit controls the switch not to pass the frequency component of the remaining noise signal of the current band when the sound pressure level of the current band is equal to or smaller than a predetermined value than the sound pressure level of a lower adjacent band, or when the sound pressure level of the current band is equal to or smaller than a predetermined value than the sound pressure level of a higher adjacent band.

4. The active silencer according to claim 3, wherein the sound quality evaluation unit analyzes a frequency of the remaining noise signal, and calculates a difference in sound pressure level between adjacent bands of the remaining noise signal divided by the first band division unit.

5. The active silencer according to claim 3, further comprising a threshold change unit to change the threshold depending on a sound pressure level for each band of the remaining noise signal.

6. The active silencer according to claim 5, wherein the threshold change unit changes the threshold to be used in determining a band into a smaller value if the sound pressure level of the band is equal to or larger than a predetermined value when the sound pressure level of the remaining noise is outstanding in the band, and changes the threshold to be used in determining a band into a larger value if the sound pressure level of the band is smaller than the predetermined value when the sound pressure level of the remaining noise is outstanding in the band.

7. The active silencer according to claim 5, wherein the threshold change unit changes the threshold to be used in determining a band into a smaller value when the band having an outstanding sound pressure level of the remaining noise refers to high sensitivity to human ears.

8. A method for controlling an active silencer comprising:

a step of detecting noise remaining after interfering with control sound as a remaining noise signal;

a step of evaluating sound quality of the remaining noise and outputting a result of the sound quality evaluation;

an actuation signal determining step of determining, according to the result of the sound quality evaluation, detection timing of a frequency component of a remaining noise signal to be used when the control sound is generated for a plurality of bands of the remaining noise, corresponding to the plurality of bands of a reference signal corresponding to the noise; and a control signal generating step of generating and outputting a control signal for generation of the control sound depending on a plurality of bands of the determined remaining noise signal and a plurality of bands of the reference signal corresponding to the noise.

9. The method for controlling the active silencer according to claim 8, wherein in the actuation signal determining step, for each band of a remaining noise signal detected at a current time point, it is determined as to whether or not the frequency component is to be passed through for use in generating the control sound by switching a plurality of switches depending on the result of the sound quality evaluation.

* * * * *